(12) United States Patent
Quinn et al.

(10) Patent No.: US 12,102,758 B2
(45) Date of Patent: *Oct. 1, 2024

(54) METHOD AND SYSTEM FOR TREATING CENTRAL SLEEP APNEA

(71) Applicant: Periodic Breathing, LLC, Baltimore, MD (US)

(72) Inventors: Jeff Quinn, Carmel, IN (US); Robert O. C. duBois, Glen Arm, MD (US); Robert W. Daly, Providence, RI (US)

(73) Assignee: Periodic Breathing. LLC, Baltimore, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/640,563

(22) Filed: Apr. 19, 2024

(65) Prior Publication Data

US 2024/0261525 A1   Aug. 8, 2024

Related U.S. Application Data

(63) Continuation of application No. 18/217,771, filed on Jul. 3, 2023, now Pat. No. 11,986,594.

(60) Provisional application No. 63/358,247, filed on Jul. 5, 2022, provisional application No. 63/434,272, filed on Dec. 21, 2022.

(51) Int. Cl.
*A61M 16/00* (2006.01)
*A61M 16/06* (2006.01)

(52) U.S. Cl.
CPC ........ *A61M 16/06* (2013.01); *A61M 16/0003* (2014.02); *A61M 16/024* (2017.08); *A61M 2016/0042* (2013.01); *A61M 2230/202* (2013.01)

(58) Field of Classification Search
CPC ...... A61M 16/0045; A61M 2202/0225; A61M 16/205; A61M 16/024; A61M 16/202
See application file for complete search history.

(56) References Cited

U.S. PATENT DOCUMENTS

| 6,098,622 A * | 8/2000 | Nobile ................ A61M 16/207 128/205.24 |
| 2008/0302364 A1* | 12/2008 | Garde ................ A61M 16/026 128/204.23 |

* cited by examiner

*Primary Examiner* — Margaret M Luarca (57) ABSTRACT

Systems and methods for controlling breathing of a patient to maintain specified levels of CO2 in arterial blood. In one exemplary embodiment a respiratory conduit is configured to be coupled at one end to a patient interface device that is, in turn, coupled to the patient's breathing airway. The respiratory conduit is configured at the opposing end to be coupled to a pressurized air generating device. A control device is positioned in the respiratory conduit between the patient interface device and the pressurized air generating device and includes one or more vent apertures that allow a predetermined amount of exhaled air from the patient to escape from the respiratory conduit while retaining a predetermined fraction of the exhaled air to reintroduce to the patient during the next inhale. In this manner the system provides for a predetermined percentage of CO2 to be rebreathed by the patient.

19 Claims, 14 Drawing Sheets

METHOD AND SYSTEM FOR TREATING CENTRAL SLEEP APNEA

CROSS-REFERENCE TO RELATED APPLICATIONS

This application is a continuation of U.S. patent application Ser. No. 18/217,771, filed Jul. 3, 2023; which claims priority from:
U.S. Provisional App. 63/358,247, filed Jul. 5, 2022; and
U.S. Provisional App. 63/434,272, filed Dec. 21, 2022,
the contents of which are incorporated entirely herein by reference.

BACKGROUND OF THE DISCLOSURE

The present disclosure relates generally to an improved method and system for the treatment of breathing disorders. In particular, the present disclosure relates to systems and methods for controlling breathing of a patient by maintaining specific levels of carbon dioxide ("$CO_2$") dissolved in the patient's arterial blood.

Sleep-disordered breathing ("SDB") includes all syndromes that pose breathing difficulties during sleep. These include obstructive sleep apnea ("OSA"), mixed sleep apnea ("MSA"), central sleep apnea ("CSA"), Cheyne-Stokes respiration ("CSR"), and others. Some form of SDB occurs in approximately 3-5% of the U.S. population.

While anatomical problems such as obesity or an abnormally narrow upper airway may be a cause of some SDB, neurological difficulties in controlling levels of blood gases, such as $CO_2$ and oxygen ("$O_2$"), are increasingly being recognized as important contributors to the SDB disease process. This is especially true of the "central" syndromes, such as MSA, CSA and CSR, which may collectively account for as much as 20% of all SDB. Changes in the neurological system that controls the blood gases often produce unsteady respiratory patterns that in turn cause arousals from sleep. These arousals are accompanied by severe spikes in blood pressure and release of stress hormones that may result in long-term damage to a number of organ systems. Additionally, some SDB syndromes involve abnormal overall levels of blood gases. For example, low levels of dissolved $CO_2$ in arterial blood are frequently encountered, which represents a clinical problem. Thus, there is a need to stabilize respiration and establish appropriate blood gas levels by restoring normal control of blood gases when treating SDB.

SUMMARY OF THE DISCLOSURE

In accordance with the present disclosure systems and methods for controlling breathing of a patient are provided to maintain specified levels of $CO_2$ in arterial blood. The systems and methods can be used to rectify inappropriate levels of both $CO_2$ and $O_2$ in arterial blood.

In one exemplary embodiment, the system is a respiratory conduit. The respiratory conduit is configured to be coupled at one end to a patient interface device that is, in turn, coupled to the patient's breathing airway, e.g., nose, mouth or both. The respiratory conduit is configured at the opposing end to be coupled to a pressurized air generating device. A control device is positioned in the respiratory conduit between the patient interface device and the pressurized air generating device.

The control device has an interior volume in fluid communication with the respiratory conduit such that air from the air generating device and exhaled air from the patient both flow into the volume. The control device further includes one or more vent apertures that allow a predetermined amount of exhaled air from the patient to escape from the respiratory conduit while retaining a predetermined fraction of the exhaled air to reintroduce to the patient during the next inhale. In this manner the system provides for a predetermined percentage of $CO_2$ to be rebreathed by the patient.

In an alternate exemplary embodiment, the system is a respiratory conduit. The respiratory conduit is configured to be coupled at one end to a patient interface device that is, in turn, coupled to the patient's breathing airway, e.g., nose, mouth or both. The respiratory conduit is configured at the opposing end to be coupled to a pressurized air generating device. A control device is positioned in the respiratory conduit between the patient interface device and the pressurized air generating device.

The control device has a vent path in fluid communication with the respiratory conduit such that air from the air generating device and exhaled air from the patient both flow into the control device. The control device further includes one or more vent apertures that allow a predetermined amount of exhaled air from the patient to escape from the respiratory conduit while retaining a predetermined fraction of the exhaled air to reintroduce to the patient during the next inhale. In this manner the system provides for a predetermined percentage of $CO_2$ to be rebreathed by the patient.

It is therefore an object of the present disclosure to provide a method and system that maintains specified levels of $CO_2$ in a patient's arterial blood. It is a further object of the present disclosure to provide a breathing conduit that couples between a patient's airway and an air delivery system such that a specified amount of the patient's exhale is retained and mixed with incoming air for reuptake during the next inhale in a manner that maintains specified levels of $CO_2$ in the patient's arterial blood. It is an object of some embodiments of the present disclosure that the specified levels of $CO_2$ are maintained by a one time setting on the respiratory conduit. It is an object of further embodiments of the present disclosure that the specified levels of $CO_2$ or breathing effort are monitored via sensors that in turn adjust the setting of the respiratory conduit.

Further features and advantages of the system, as well as structure and operation of the various embodiments of the disclosure, are discussed in detail below with reference to the accompanying drawings.

BRIEF DESCRIPTION OF THE DRAWINGS

The method and system of the disclosure is described with reference to the accompanying drawings. In the drawings, like reference numbers indicate identical or functionally similar elements.

DETAILED DESCRIPTION OF THE DISCLOSURE

Now referring to the drawings, the system and method for controlling breathing is shown and generally illustrated in the figures. It is notable that of the two blood gases, carbon dioxide ("$CO_2$") and oxygen ("$O_2$"), problems with neurological control of breathing during sleep are primarily related to the control of $CO_2$ rather than $O_2$. $CO_2$ is dissolved in blood, and together with bicarbonate ions determines blood pH. Excessive $CO_2$ causes the blood to become acidic, while a deficit in $CO_2$ will cause the blood to be alkaline. Since proteins need a stable pH environment in which to function, the $CO_2$ levels should be controlled within a narrow range that will yield a blood pH of about 7.4. This is accomplished in the present invention through the close matching of $CO_2$ excretion via the lungs to the endogenous $CO_2$ production that is the product of cellular metabolism.

Figure 1:
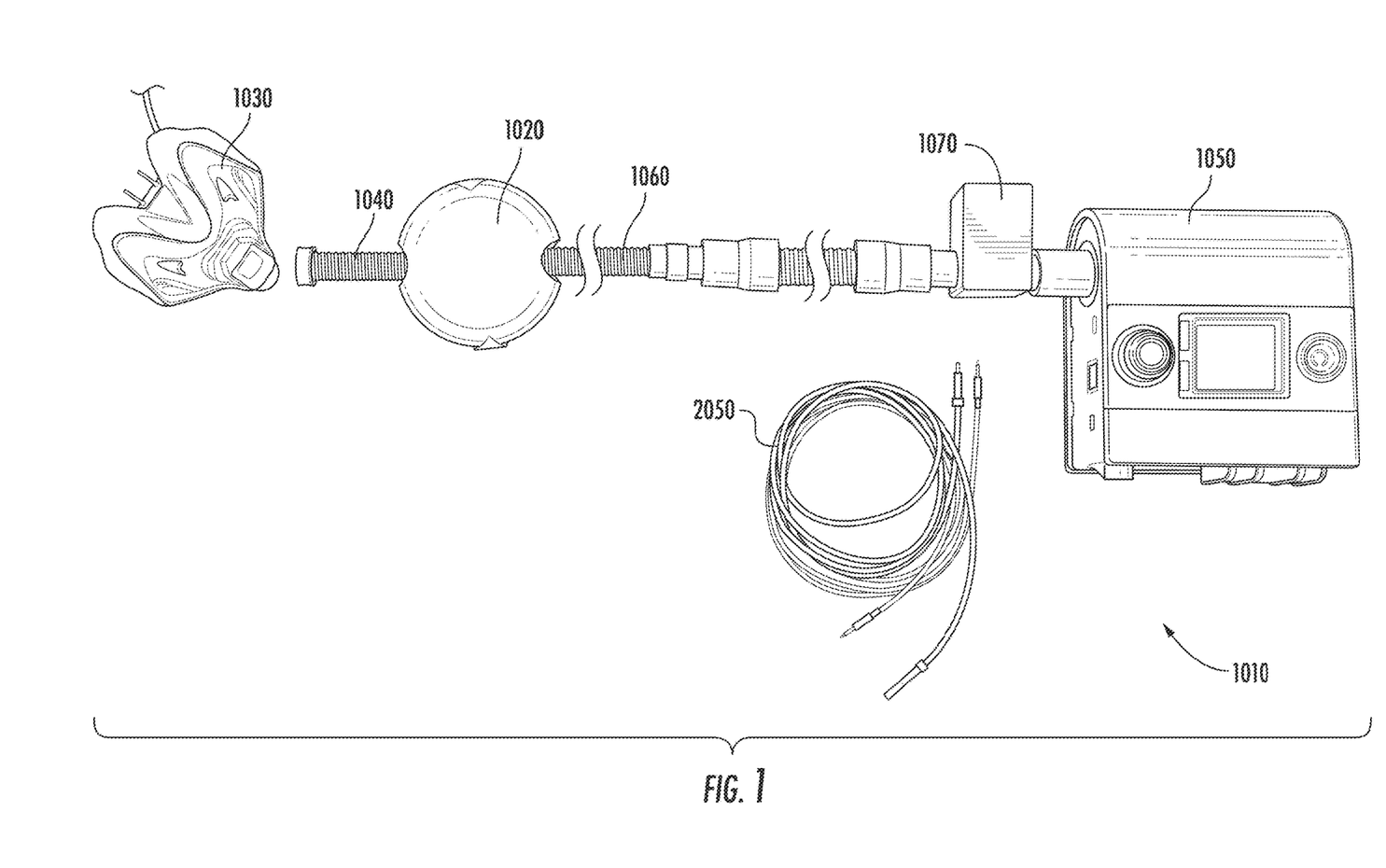
FIG. 1 is an illustration showing an exemplary system for controlling breathing of a patient, according to the present disclosure.
Figure 2:
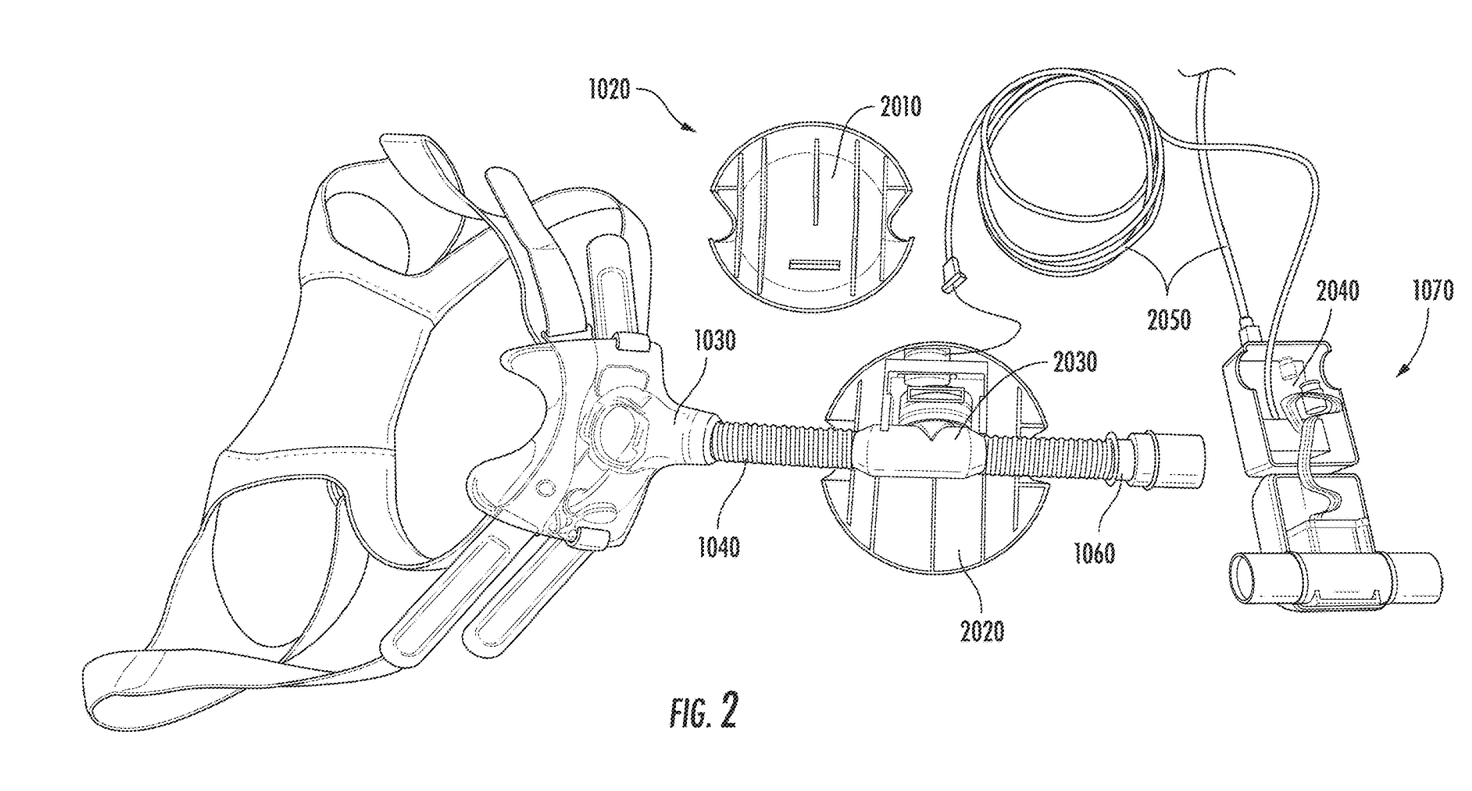
FIG. 2 is the exemplary system of FIG. 1 with a cover removed from the control device used in a respiratory conduit for controlling breathing of a patient, according to the present disclosure.

As seen at FIGS. 1 and 2, in an exemplary embodiment, the system 1010 includes a respiratory conduit 1020. The respiratory conduit 1020 is configured to be coupled at one end to a patient interface 1030 device via an upper conduit 1040. The patient interface 1030 is in turn, coupled to the patient's breathing airway, e.g., nose, mouth or both. The respiratory conduit 1020 is configured at the opposing end to be coupled to a pressurized air generating device 1050 via a lower conduit 1060. A flow/pressure monitor 1070 may further be included between the lower conduit 1060 and the pressurized air generating device 1050. As best seen in FIG. 2, the respiratory conduit 1020 has a top enclosure 2010, a bottom enclosure 2020 and a control device 2030 positioned in the respiratory conduit 1020 between the patient interface device and the pressurized air supply device. A controller 2040 is shown positions within the flow pressure monitor 1070 but may be alternately positions within the respiratory conduit 1020, in a separate dedicated enclosure or any other suitable position within the system of the present disclosure. Connecting wires 2050 are employed as needed to allow control and communication as between the control device 2030 the controller 2040, the pressure monitor 1070 and any other devices that interface with the system.

Figure 3:
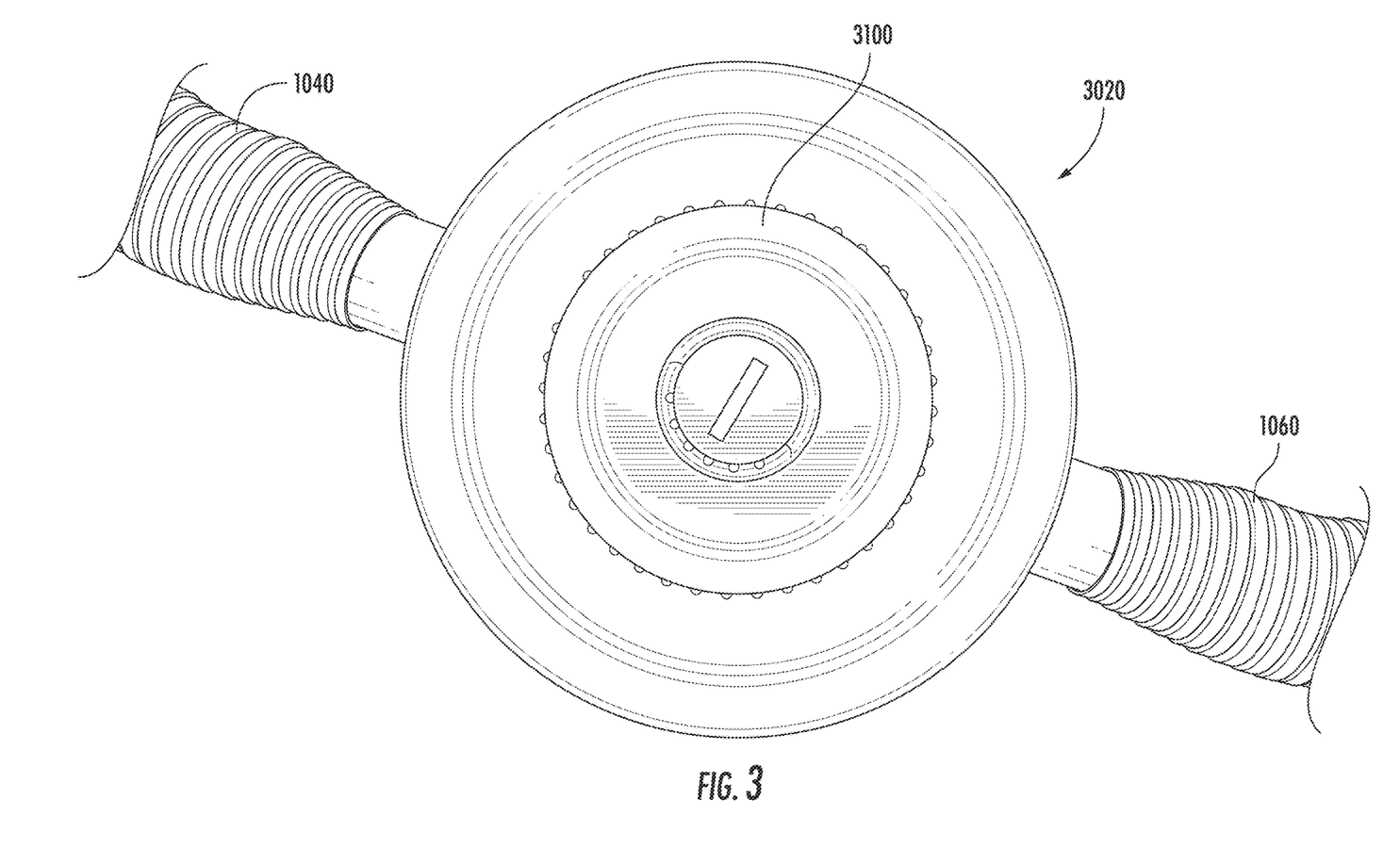
FIG. 3 is an exemplary control device.

As shown in FIG. 3 one illustrative embodiment of the respiratory conduit 3020 contains therein a controlled volume and a control device 3100. Rates of flow of a gas through the control device 3100 positioned in the respiratory conduit 3020 are calculated based on an expected rate of production of the gas by the patient, expected respiration rate of the patient, expected depth of respiration by the patient, and an expected concentration of the gas in the air expired by the patient.

Figure 4:
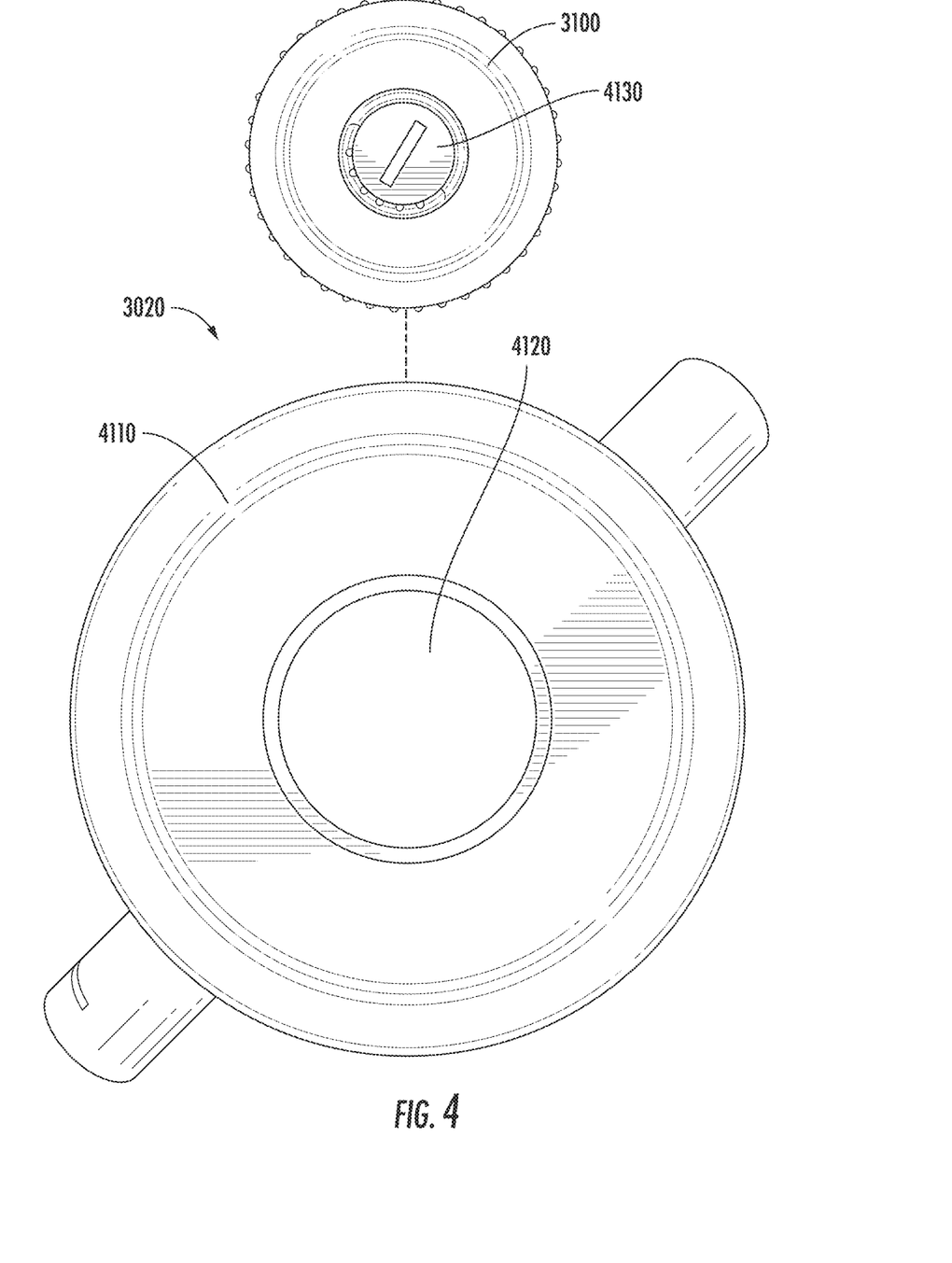
FIG. 4 is the control device of FIG. 3 with the control aperture removed

Turning now to FIG. 4, the respiratory conduit 3020 has a shell 4110 enclosing an interior volume 4120 in fluid communication with the respiratory conduit such that air from the air generating device and exhaled air from the patient both flow into the interior volume 4120. The control device 3100 further includes one or more vent apertures positioned in a control aperture dial 4130 that allow a predetermined amount of exhaled air from the patient to escape from the respiratory conduit while retaining a predetermined fraction of the exhaled air to reintroduce to the patient during the next inhale. In this manner the system provides for a predetermined percentage of $CO_2$ to be rebreathed by the patient.

Figure 5A:
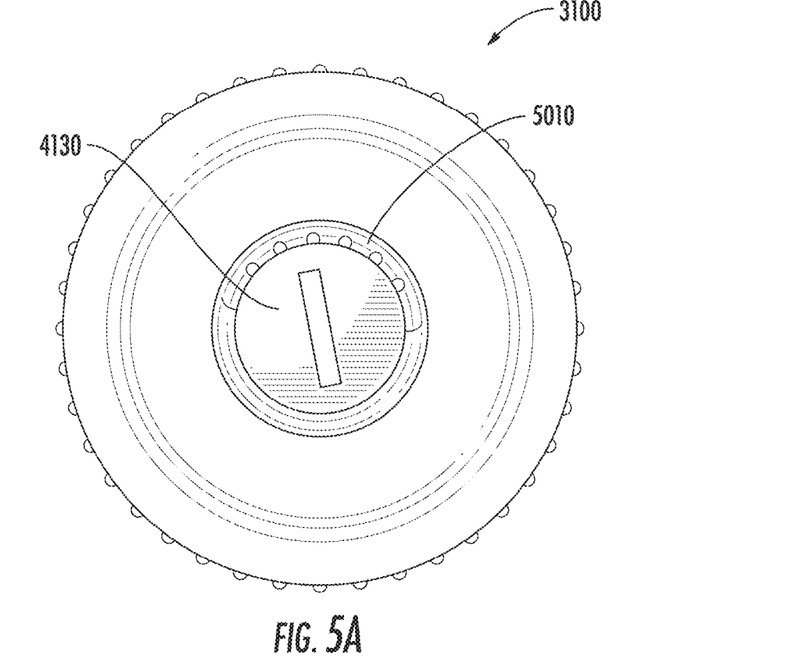
FIG. 5A is the control aperture of FIG. 3 set to allow more $CO_2$ escape/less patient $CO_2$ rebreathing.
Figure 5B:
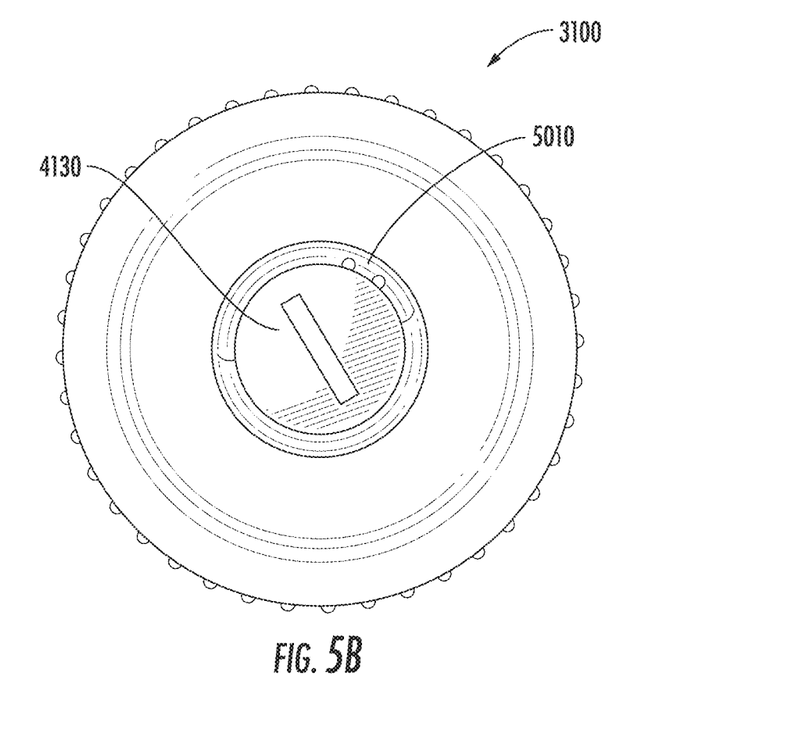
FIG. 5B is the control aperture of FIG. 3 set to allow less $CO_2$ escape/more patient $CO_2$ rebreathing.

As seen at FIGS. 5a and 5b the control aperture dial 4130 has a plurality of sized apertures 5010 therein. The control dial aperture 4130 can be rotated to expose or close one or more of the apertures 5010 thereby allowing more (FIG. 5A) or less (FIG. 5B) of the mixed exhale and supply air to escape therefrom. Based on the determined level of $CO_2$ to be supported the control aperture dial 4130 is set such that a predetermined amount of $CO_2$ is maintained during each breath thereby retaining a set concentration of $CO_2$ in the respiratory conduit for the patient to rebreathe in the next inhale.

Figure 6:
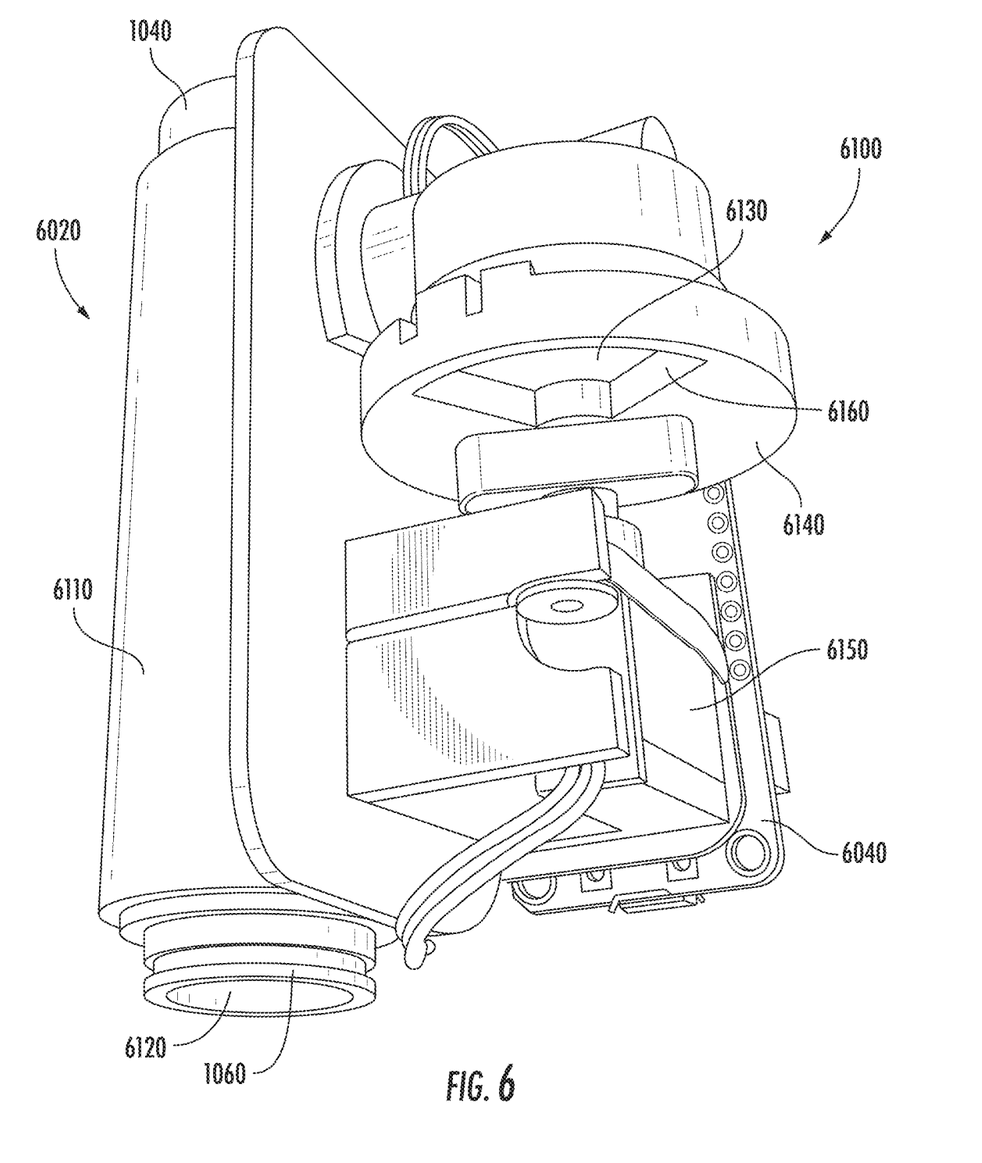
FIG. 6 is an illustration showing an alternate exemplary respiratory conduit for controlling breathing of a patient, according to the present disclosure.

As seen at FIG. 6, in an alternate exemplary embodiment, the system is a 6020 respiratory conduit. The respiratory conduit 6020 is configured to be coupled at one end 1040 to a patient interface device that is, in turn, coupled to the patient's breathing airway, e.g., nose, mouth or both. In this case, the respiratory conduit may be coupled directly to the outlet on a sealed breathing mask. The respiratory conduit is configured at the opposing end 1060 to be coupled to a pressurized air generating device. A control device 6100 is positioned in the respiratory conduit 6020 between the patient interface device and the pressurized air supply device.

Figure 7:
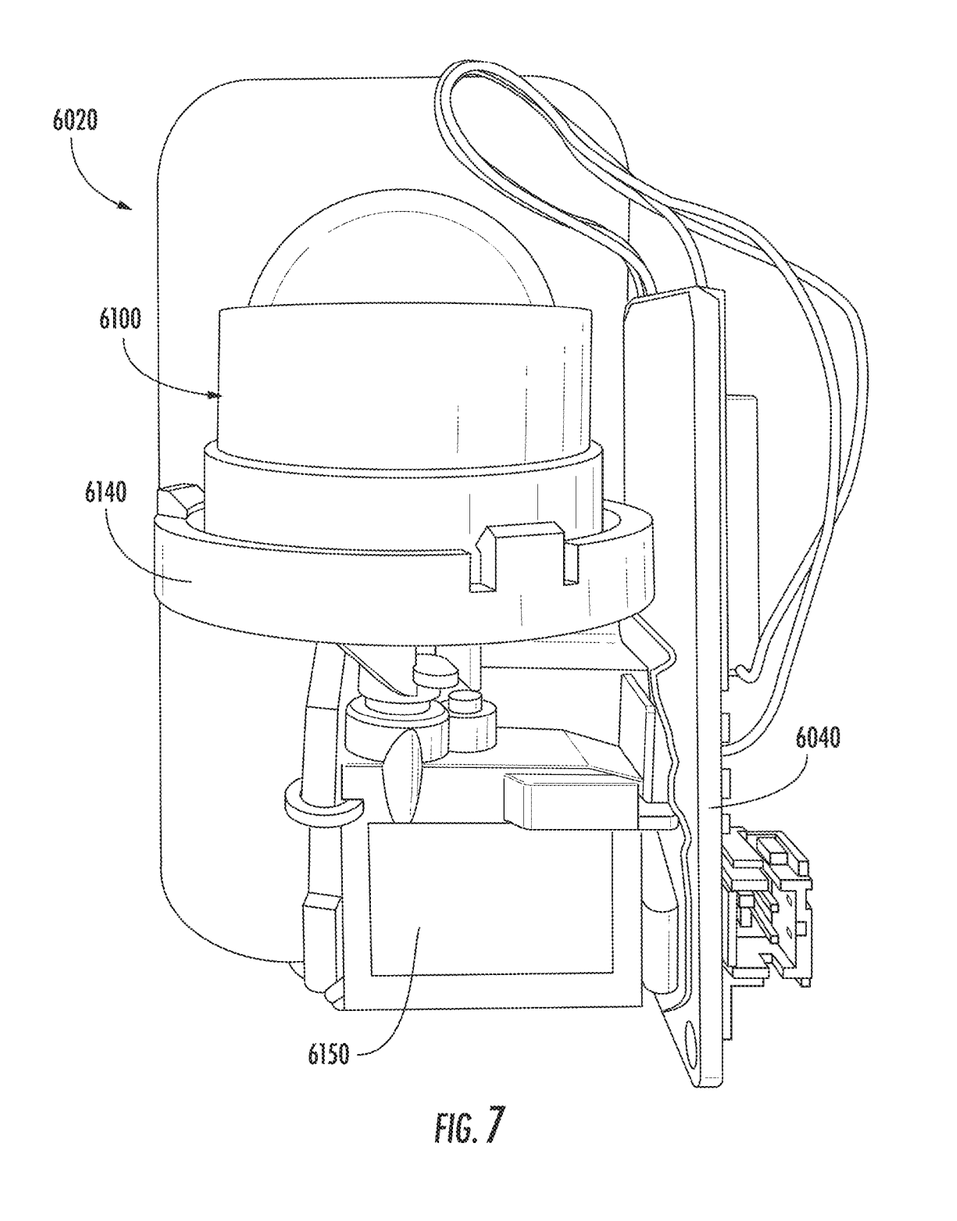
FIG. 7 is an alternate view of the exemplary respiratory conduit for controlling breathing of a patient of FIG. 5, according to the present disclosure.
Figure 8:
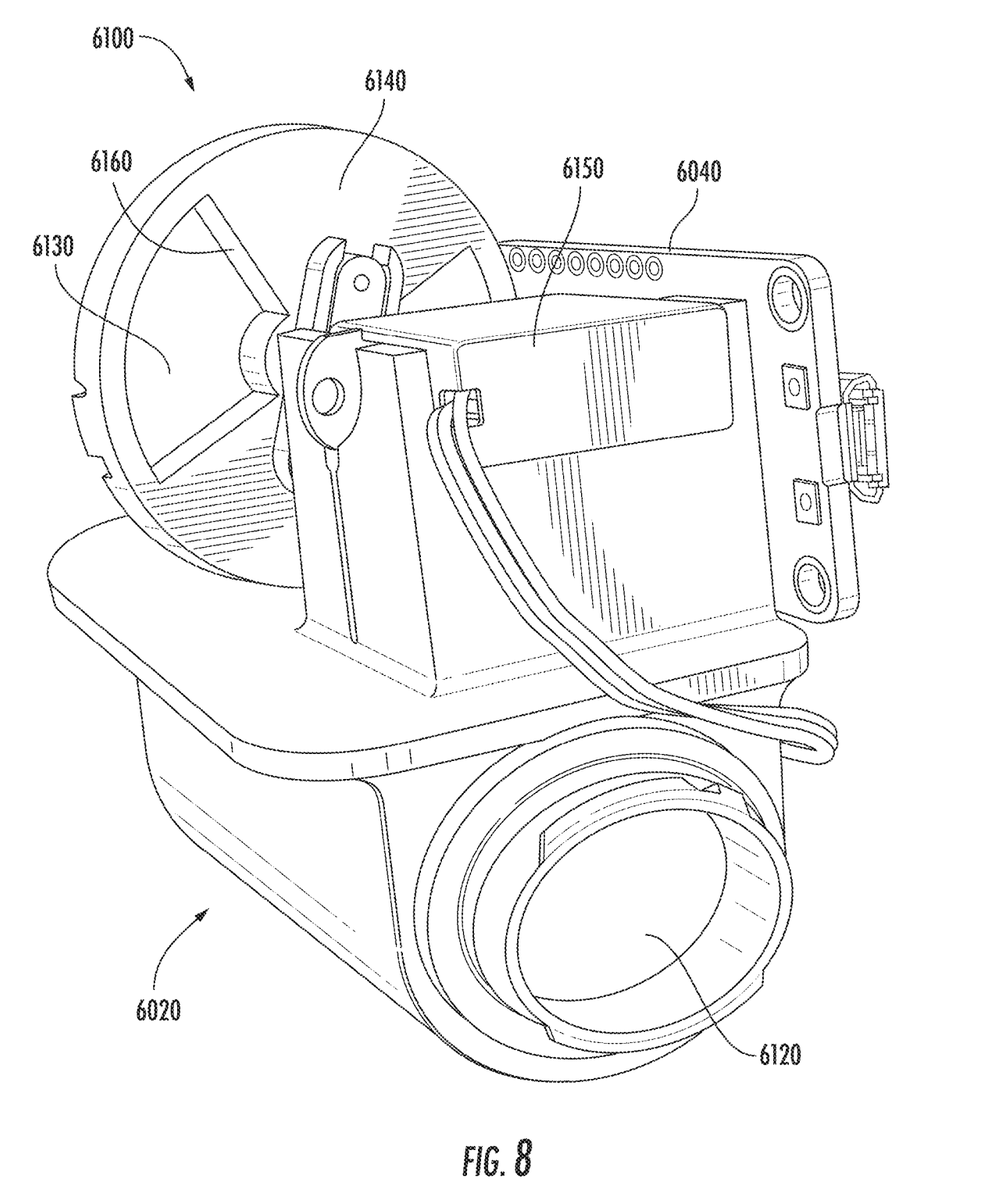
FIG. 8 is a second alternate view of the exemplary respiratory conduit for controlling breathing of a patient of FIG. 5, according to the present disclosure.

The respiratory conduit includes a control aperture dial 6130. Rates of flow of a gas through the control device positioned in the respiratory conduit are calculated based on an expected rate of production of the gas by the patient, expected respiration rate of the patient, expected depth of respiration by the patient, and an expected concentration of the gas in the air expired by the patient. Using this information, the control aperture dial 6130 is set by stepper motor 6150 based on commands from controller 6040 to a baseline position relative to the vent cover 6140 that allows exhaust of a predetermined amount of $CO_2$ for a patient's exhaled breath through a plurality of apertures that are aligned with vent opening 6160 in the vent cover 6140. As seen in the combination of FIGS. 6, 7 and 8, a position of the control aperture dial 6130 is set by a small servo/stepper motor 6150 that is in turn controlled by circuitry on the control board 6040 mounted adjacent to the servo/stepper motor and in electrical communication therewith.

A sensor is employed to monitor changes in respiratory rhythm and/or effort of the patient based on changes within the respiratory conduit. The changes monitored may include pressure, breathing effort and/or breathing rhythm. An algorithm monitors changes detected and compares those changes to patient baseline respiratory data to identify apnea events and disordered breathing. The change monitor(s) are also in electrical communication with the control board and the algorithm may operate in a processor on the control board or a remote processor in communication with the control board.

Figure 9A:
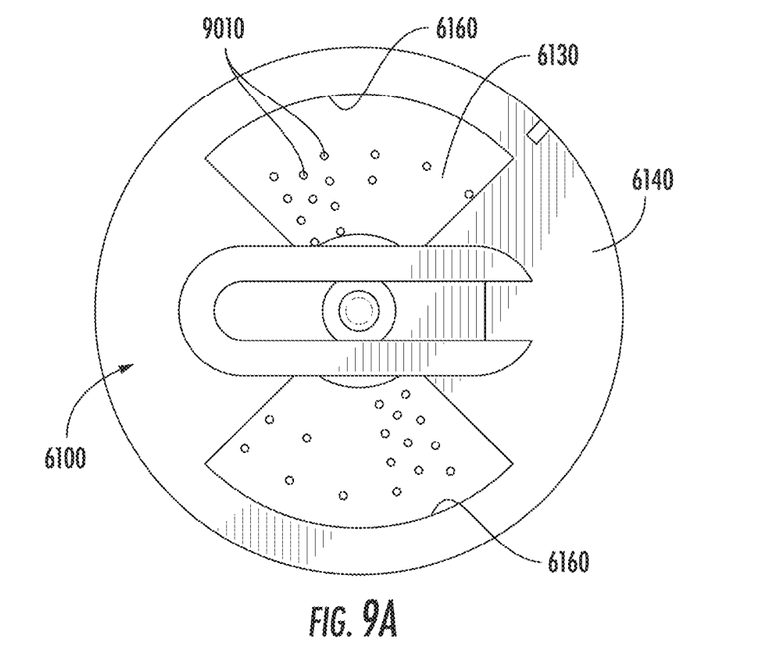
FIG. 9A is the control aperture of FIG. 6 set to allow more $CO_2$ escape/less patient $CO_2$ rebreathing.
Figure 9B:
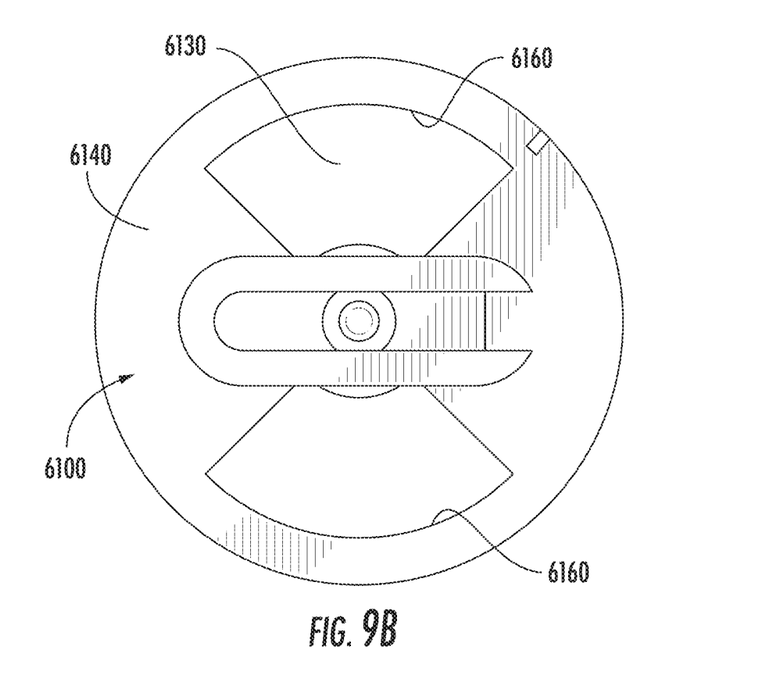
FIG. 9B is the control aperture of FIG. 6 set to allow less $CO_2$ escape/more patient $CO_2$ rebreathing.
Figure 10:
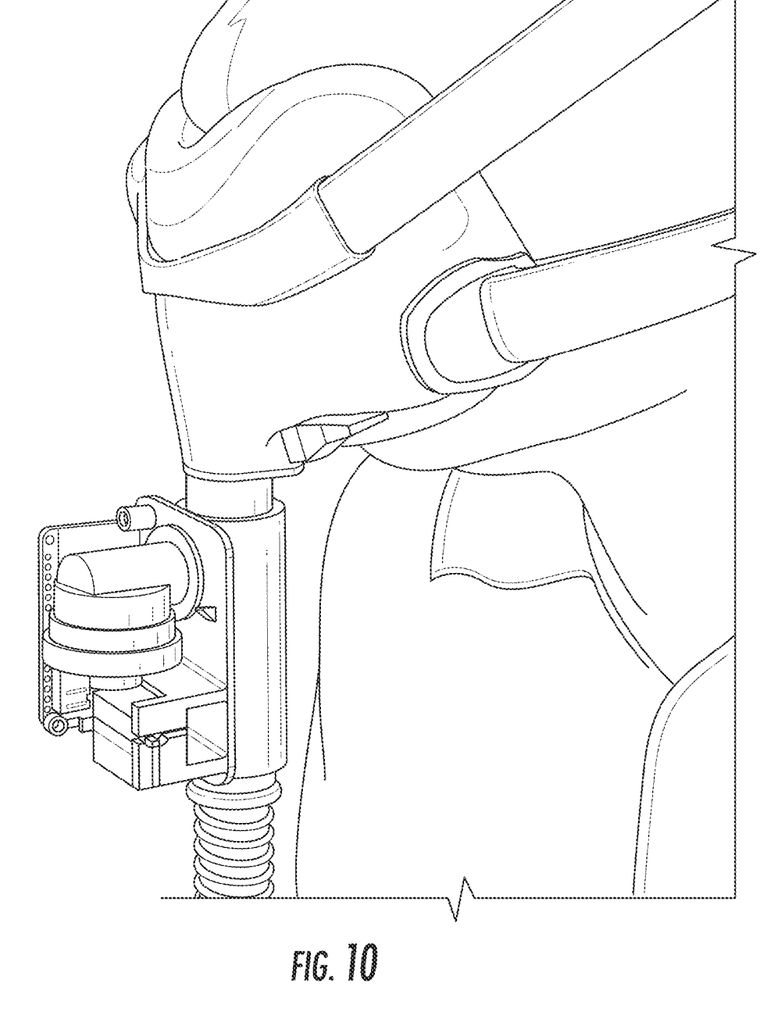
FIG. 10 is an illustration of the patient interface portion of the system of the present disclosure.

Turning now to FIGS. 9A and 9B, as stated above, the control device has an interior volume in fluid communication with the respiratory conduit such that air from the air generating device and exhaled air from the patient both flow into the volume. The control device further includes a control aperture dial 6130 with one or more vent apertures 9010 positioned in the control aperture dial 6130 that allow a predetermined amount of exhaled air from the patient to escape from the respiratory conduit while retaining a predetermined fraction of the exhaled air to reintroduce to the patient during the next inhale. The control over the predetermined amount of exhaled air is varied by rotation of the vent cover 6140 wherein, as shown in FIG. 9B, vent openings 6160 in the vent cover 6140 are positioned such that vent apertures 9010 are exposed allowing the escape of more exhaled air. At FIG. 9B the vent cover 6140 is positioned such that the vent openings 6160 are not aligned and the vent apertures 9010 are covered retaining more of the exhaled air. It should be appreciated by one skilled in the art that such control is gained by the relative positioning between the control aperture dial 6130 and the vent cover 6140 and that such relative positioning may be accomplished by rotating either of the control aperture dial 6130 or the vent cover 6140 or both to gain the desired relative positioning. Further, it can be seen that the vent cover 6140 may include one or more vent openings 6160 and still remain within the scope of the disclosure. In this manner the system provides for a predetermined percentage of CO2 to be rebreathed by the patient.

The control aperture dial has a plurality of sized apertures therein. A vent cover positioned above the control aperture can be rotated to expose or close one or more of the apertures thereby allowing more or less of the mixed exhale and supply air to escape therefrom. Based on the determined level of CO2 to be supported the control dial is set such that a predetermined amount of CO2 is maintained during each breath thereby retaining a set concentration of CO2 in the respiratory conduit for the patient to rebreathe in the next inhale.

It should be appreciated that rotation of the control aperture dial is intended to allow venting of more or less CO2. Therefore, while multiple apertures are shown, it is within the scope of the present disclosure that at least one larger aperture or several smaller apertures may be used. The feature primarily includes a total venting area which is the area of the total exposed, functional venting aperture(s) that is controlled by rotation of the control aperture vent dial.

Figure 11:
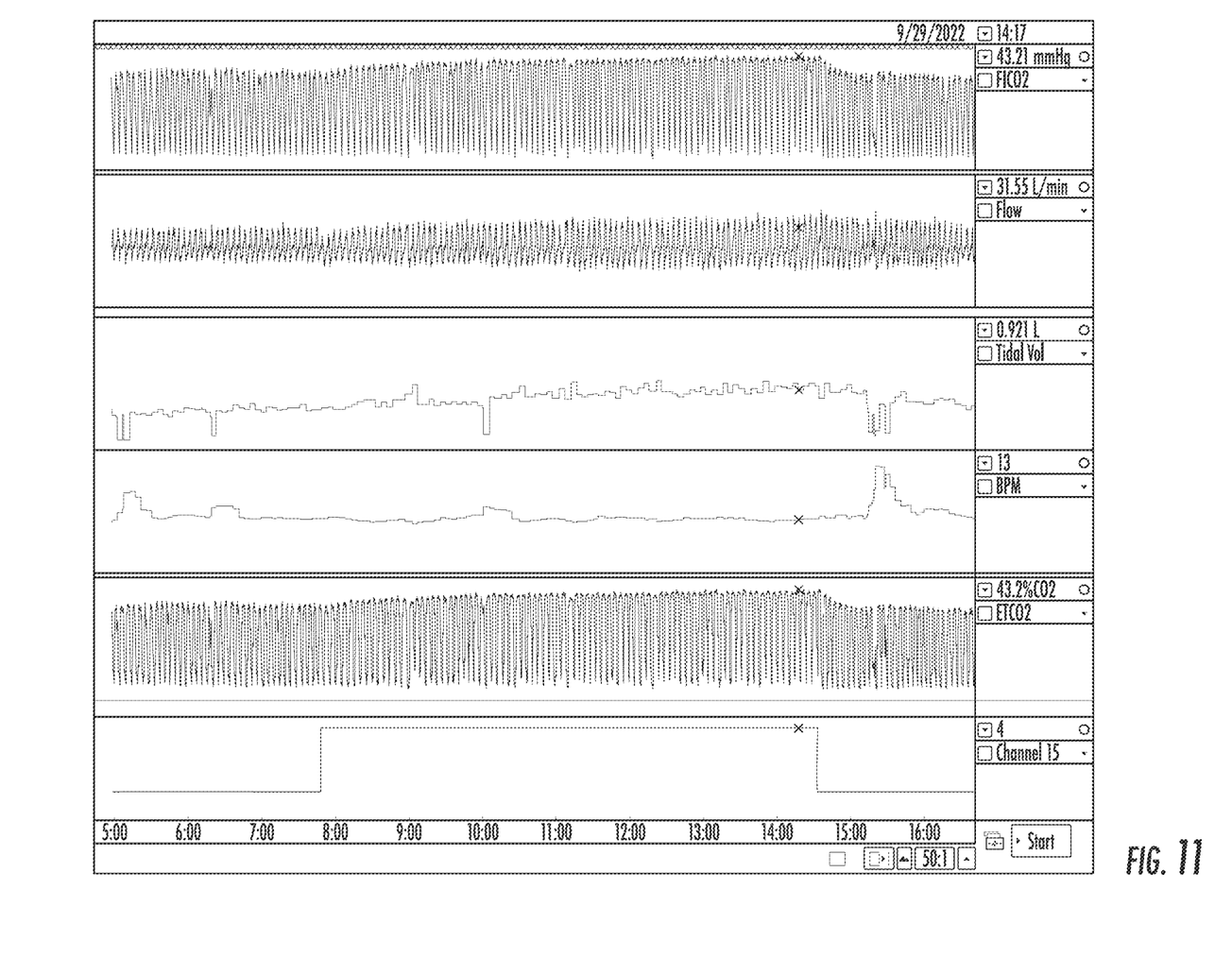
FIG. 11 is a graph showing a healthy adult breathing via the present system, with a CPAP pressure of 5 cm $H_2O$.
Figure 12:
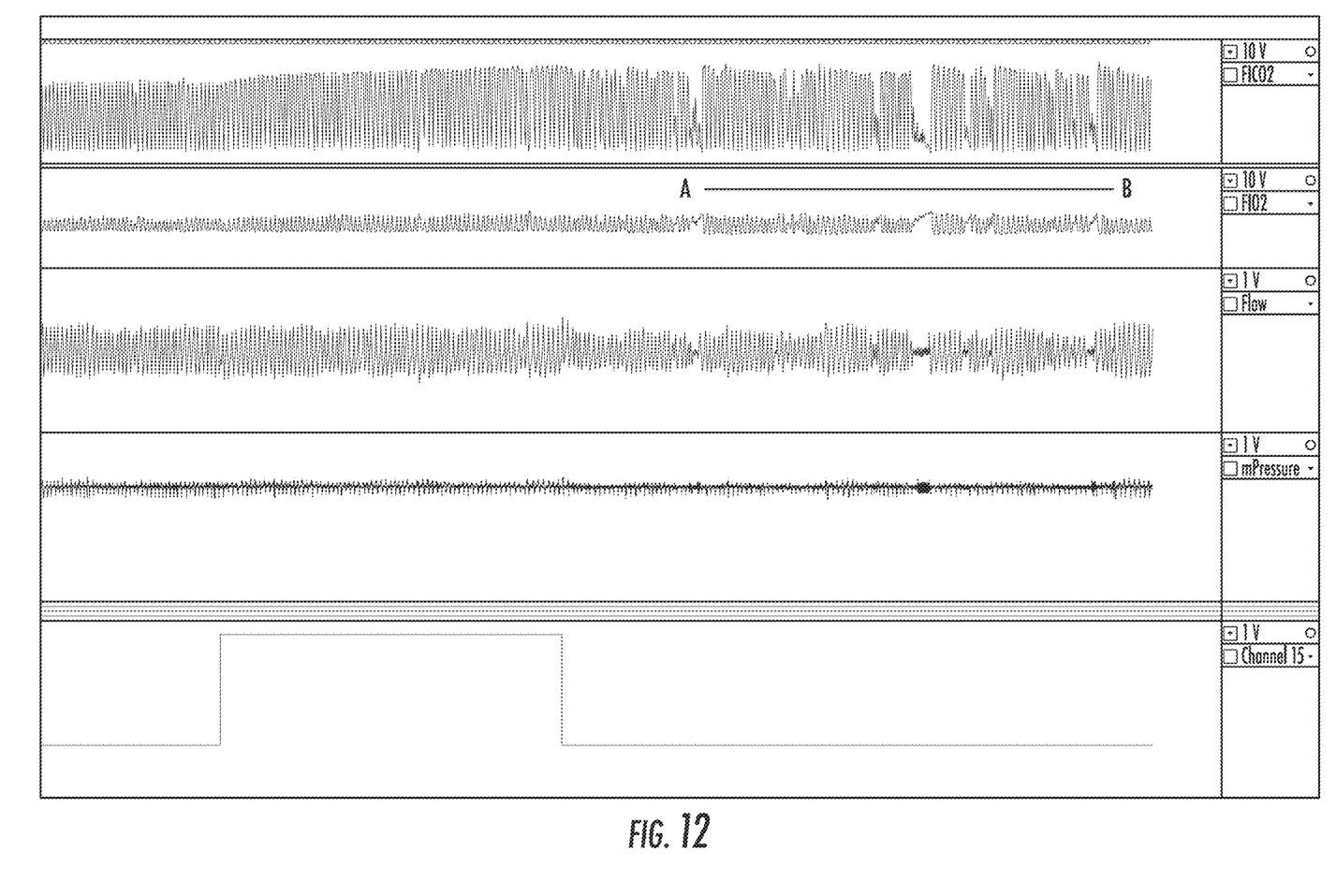
FIG. 12 is a graph of the breathing of a subject showing a few mild apneas on the right side of the plot.
Figure 13:
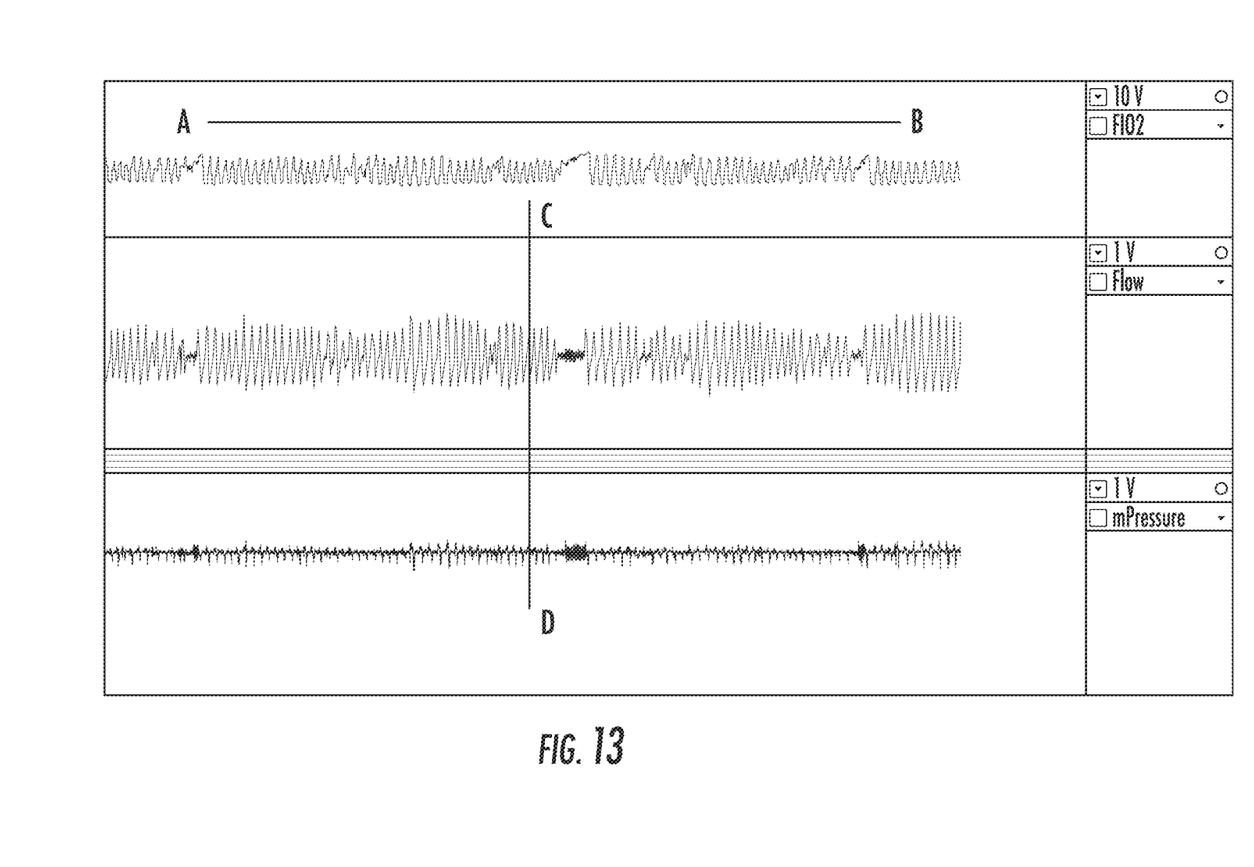
FIG. 13 is a graph of the breathing of a subject showing both mild and significant apneas.

FIGS. 11-13 depict detection of unstable breathing patterns that consist of alternating hyperventilation and hypoventilation or apnea. During hyperventilation, there is rapid "blow-off" of CO2 that causes a steep drop in arterial CO2 that initiates an epoch of hypoventilation or even apnea when the arterial blood reaches the peripheral chemoreceptor and the brain detects an abnormally low level of blood CO2. During the hypoventilation, CO2 accumulates rapidly and again initiates an epoch of hyperventilation. This pattern can be repeated indefinitely. FIG. 11 shows a healthy adult breathing monitored via the device of the present disclosure, with a CPAP pressure of 5 cmH2O. In Channel 15 (bottom) the P.B. titration or valve setting is tracked. In order from left to right, FICO2, Flow, and Tidal volume rise in response to the titration level increase in Channel 15 (mid plot). These are expected normal physiologic response to increasing EtCo2.

In FIG. 12, the subject shows a few mild apneas on the right side of the plot, following decrease in titration level of EtCo2, mid-left plot in Channel 15. Along line segment AB (in FiCo2, FiO2, Flow, and mask pressure), apnea like incidents occur repeatedly and suggestive minor tremors in mask pressure and flow occur as well. The minor fluctuations in mask pressure and flow present signal recognition opportunities. So far the assumption has been that the appearance of abnormal CO2 patterns will provide a control signal to modulate CO2, and theoretically thereby moderate or prevent the apneas. CO2 sensors are expensive and somewhat slow compared to pressure sensors. The option of tracking either flow or mask pressure provides an inexpensive and fast response method by comparison.

As an example of a control loop relevant to the plot data and apneas, the signal amplitude and frequency would be monitored and deviations outside of user configurable "normal" in these would be translated by control logic to increased titration at a user configurable % of a predetermined normal CO2 production by the individual patient.

Figure 14:
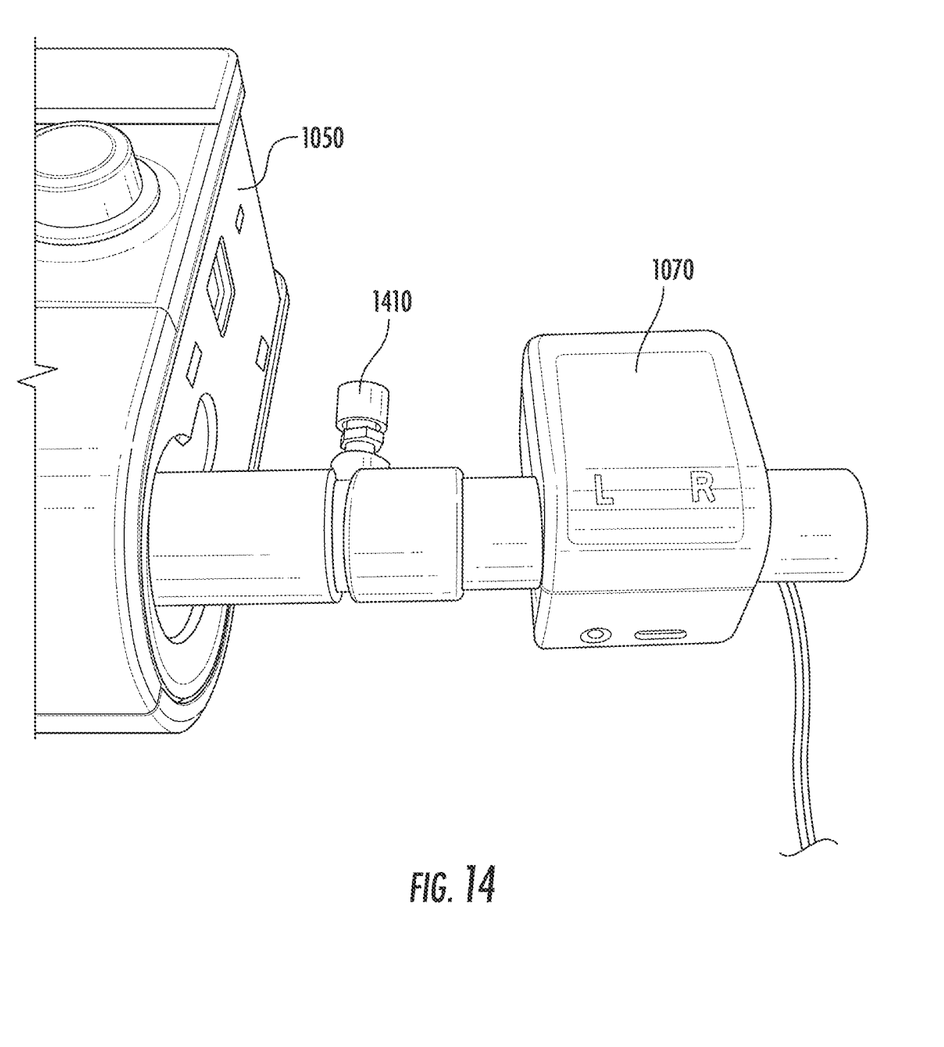
FIG. 14 depicts a pressure/flow monitor for use in connection with the system of the present disclosure.

In FIG. 13, to the left and right of vertical line segment CD, the apneas are respectively very mild or quite significant. The incidents to the right could possibly be eliminated by the control response (increased titration of Co2) initiated in response to the first mild apnea on the far left for example. Both flow as measured by the flow/pressure detector 1070 of FIG. 14 (differential pressure transducer output) and mask pressure show the occurrence of the apneas. Differential pressure is slightly more complex and cumbersome to implement in hardware. Mask pressure is relatively simple and inexpensive. Both present simple, low power, low cost signal detection options for the control of EtCo2 in response to and anticipation of apneas.

Ideally, the lungs should be made to be less efficient during hyperventilation in order to resist the CO2 blow-off. One of the ways to do this is to make the patient inhale some percentage of CO2 in inspired air, which will interfere with gas exchange in the lungs and therefore prevent excessive excretion of CO2. Likewise, the lungs should be maximally efficient during hypoventilation in order to limit the accumulation of CO2. Thus, inhaled CO2 is optimally zero during hypoventilation. Any design can be characterized in terms of its ability to exert a stabilizing influence by feeding the patient at least a fraction of inspired CO2 during hyperventilation and none during hypoventilation.

The system of the present disclosure operates on a principal that provides a variable resistance to outflow of gas at the CPAP mask, thereby varying the level of biased flow and CO2 washout from the system. Increasing degrees of CO2 rebreathing occurred in a linear, controlled fashion as the control device was progressively occluded at each of four steps. At Step 1 (baseline, i.e. typical of normally vented CPAP masks), virtually all exhaled CO2 could be vented to atmosphere, yet the control device provided sufficient resistance to maintain a set CPAP level of 5 cmH2O. Steps 2 through 4 decrease the biased flow through the CPAP breathing circuit and increase CO2 in ascending steps. Each step caused an increase in inspired CO2 (FICO2). As mentioned, the control device setting (resistance) was varied systematically to provide for variable degrees of biased flow through the CPAP breathing circuit, and hence allowed the patient to rebreathe differing amounts of their own exhaled $CO_2$ that accumulated in the circuit. The control device setting exposed a variable number of vent apertures in the control disk, and was changed by a remotely control stepper motor. The motor and circuit board report the valve setting.

Therefore, it can be seen that the $FICO_2$ can be controlled by a simplified, light-weight, variable resistance valve that is fully integrated into a standard CPAP breathing circuit. The level of $FICO_2$ varies with the rate of $CO_2$ production (due to differences in the subject's basal metabolic rate or BMI) and the resistance of the valve (and consequently, the level of biased or leak flow through the breathing circuit). It will also vary with the applied CPAP level (which will alter the bias flow and $CO_2$ washout from the breathing circuit). The valve position can be easily controlled remotely with a stepper motor in order to adjust the biased flow and $FICO_2$. This finding implies that (1) the $FICO_2$ can be readily titrated during sleep in order to optimize the therapeutic response, and that (2) the valve position can be controlled dynamically in order to: (a) compensate for inadvertent variable leaks in the breathing circuit, and (b) respond to residual Cheyne Stokes respiration.

The $CO_2$ controller mechanism provided by the present disclosure generated predictable responses in ventilation to increasing levels of $ETCO_2$, which were comparable to historic values for HCVR. This finding further validates our approach for controlling $FICO_2$ for therapeutic purposes. The magnitude of the ventilatory responses to elevations in $ETCO_2$ identify a tolerable and effective $C0_2$ range over which therapeutic responses can be achieved. As a result, the method and system of the disclosure provides a compact, tolerable, integrated mechanism for controlling $FICO_2$, and generates predictable ventilatory responses to step-changes in $FICO_2$. The system meets conditions that are both necessary and sufficient for conducting in-laboratory therapeutic testing in patients with Cheyne Stokes respiration. The findings also highlight possibilities for elaborating on the base system to respond to changes in patients' breathing patterns, CPAP requirement and variable leaks from the breathing circuit.

In other exemplary embodiments, a $CO_2$ concentration sensor may be provided on the interior volume of the control device to determine the concentration of $CO_2$ maintained within the mixed airflow in the control. In further exemplary embodiments, a pressure sensor may be provided on the interior volume of the control device to determine changes in breathing effort as compared to a patient baseline. Further, operation of the aperture control dial may be automated such that the dial is rotated to increase or decrease the area of exposed free apertures thereby allowing increase or decrease in the vented $CO_2$ from the rebreathed mixed air flow based on the $CO_2$ concentration identified by the $CO_2$ sensor or pressure changes identified by the pressure sensor and thereby set a predetermined $CO_2$ target for patient rebreathing.

In other embodiments the air supply may be a conventional CPAP, a supply air fan or any other air supply device. While in some embodiments the supply air may not be pressurized and simply be open to free environmental air. In further embodiments, supplemental oxygen may be added to the system via supply port 14010 shown in FIG. 14.

The system of the present disclosure forces an increase in the depth of breathing and, thus, the overall rate of ventilation, since the control device is configured to saturate at a level that is insufficient to permit excretion of all $CO_2$ being produced by the patient. The patient breathes deeply enough to push $CO_2$ through the control device volume, so that $CO_2$ exits the device through the control dial apertures. By the time patient's inspiratory interval commences, the exhaled gas in control device volume has been replaced at least partially with supply air and, thus, the concentration of oxygen in the inspired air is only slightly lower than that in the ambient air. Taking the two things together, the increase in breathing more than offsets the slight decline in oxygen content of inspired air ($FIO_2$) to produce greater oxygen transport in the lungs.

It can therefore be seen that the present disclosure provides a method and system that maintains specified levels of $CO_2$ in a patient's arterial blood. Further, the present disclosure provides a breathing conduit that couples between a patient's airway and an air delivery system such that a specified amount of the patient's exhale is retained and mixed with incoming air for reuptake during the next inhale in a manner that maintains specified levels of $CO_2$ in the patient's arterial blood. Still further some embodiments of the present disclosure provide that the specified levels of $CO_2$ are maintained by a onetime setting on the respiratory conduit. In still further embodiments the present disclosure provides that the specified levels of $CO_2$ are monitored via sensors that in turn adjust the setting of the respiratory conduit. In yet a further embodiment the present disclosure provides that the specified levels of breathing effort are monitored via sensors that in turn adjust the setting of the respiratory conduit.

Example embodiments of the methods, circuits, and components of the present invention have been described herein. As noted elsewhere, these example embodiments have been described for illustrative purposes only and are not limiting. Other embodiments are possible and are covered by the invention. Such embodiments will be apparent to persons skilled in the relevant art(s) based on the teachings contained herein. Thus, the breadth and scope of the present invention should not be limited by any of the above-described exemplary embodiments, but should be defined only in accordance with the following claims and their equivalents.

What is claimed:

1. A system for controlling the breathing of a patient comprising:
   a respiratory conduit having first and second ends, a cavity defined there between and an opening in said cavity between said first and second ends; and
   a control device containing a controlled interior volume, said controlled volume being outside said respiratory conduit and in fluid communication with an airflow within said cavity via said opening,
   wherein a controlled amount of a patient's exhaled breath passes through said opening into said controlled volume,
   wherein said control device operates to regulate the release of a controlled amount of a patient's exhaled carbon dioxide.

2. The system of claim 1, the control device further comprising:
   a control aperture dial with a plurality of apertures therein, said apertures allowing a predetermined amount of exhaled breath from the patient to escape from the controlled volume while retaining a predetermined fraction of the exhaled breath to reintroduce to the patient during the next inhale.

3. The system of claim 2, wherein said predetermined fraction of reintroduced exhaled breath is determined based on a calculated percentage of $CO_2$ to be rebreathed by the patient.

4. The system of claim 2, the control device further comprising:
a vent cap adjacent said control aperture dial, said vent cap having at least one vent opening therein.

5. The system of claim 4, wherein said vent cap is rotatable relative to said control aperture dial having a closed position wherein said at least one vent opening is positioned away from said apertures, an open position wherein said at least one vent opening is positioned in alignment with said apertures and a range of intermediate positions between said open and closed positions where said vent opening is in alignment with a predetermined number of said apertures, the position of said vent cap relative to said apertures regulating the release of a controlled amount of a patient's exhaled breath.

6. The system of claim 5, wherein said predetermined fraction of reintroduced exhaled breath is determined based on a calculated percentage of $CO_2$ to be rebreathed by the patient.

7. The system of claim 4, wherein said control aperture dial is rotatable relative to said vent cap having a closed position wherein said at least one vent opening is positioned away from said apertures, an open position wherein said at least one vent opening is positioned in alignment with said apertures and a range of intermediate positions between said open and closed positions where said vent opening is in alignment with a predetermined number of said apertures, the position of said apertures in said control aperture dial relative to said at least one vent opening regulating the release of a controlled amount of a patient's exhaled breath.

8. The system of claim 7, wherein said predetermined fraction of reintroduced exhaled breath is determined based on a calculated percentage of $CO_2$ to be rebreathed by the patient.

9. The system of claim 1, further comprising:
a controller; and
a flow volume detector connected to said controller,
wherein said flow volume detector and said controller operate to predict apnea events based on a change in volume of said patient's exhaled breath,
wherein said controller operates said control device to change the amount of release in response to said apnea event.

10. The system of claim 9 further comprising:
a stepper motor operably connected to said control device to control a position of said control device based on an instruction from said controller.

11. The system of claim 10, wherein said predetermined fraction of reintroduced exhaled breath is determined based on a calculated percentage of $CO_2$ to be rebreathed by the patient.

12. The system of claim 10, the control device further comprising:
a vent cap adjacent said control aperture dial, said vent cap having at least one vent opening therein.

13. The system of claim 12, wherein said vent cap is rotatable relative to said control aperture dial having a closed position wherein said at least one vent opening is positioned away from said apertures, an open position wherein said at least one vent opening is positioned in alignment with said apertures and a range of intermediate positions between said open and closed positions where said vent opening is in alignment with a predetermined number of said apertures, the position of said vent cap relative to said apertures regulating the release of a controlled amount of a patient's exhaled breath.

14. The system of claim 13, wherein said predetermined fraction of reintroduced exhaled breath is determined based on a calculated percentage of $CO_2$ to be rebreathed by the patient.

15. The system of claim 12, wherein said control aperture dial is rotatable relative to said vent cap having a closed position wherein said at least one vent opening is positioned away from said apertures, an open position wherein said at least one vent opening is positioned in alignment with said apertures and a range of intermediate positions between said open and closed positions where said vent opening is in alignment with a predetermined number of said apertures, the position of said apertures in said control aperture dial relative to said at least one vent opening regulating the release of a controlled amount of a patient's exhaled breath.

16. The system of claim 15, wherein said predetermined fraction of reintroduced exhaled breath is determined based on a calculated percentage of $CO_2$ to be rebreathed by the patient.

17. A method for controlling the breathing of a patient comprising:
providing a respiratory conduit having first and second ends, a cavity defined there between and an opening in said cavity between said first and second ends, and, a control device containing a controlled interior volume, said controlled volume being outside said respiratory conduit and in fluid communication with an airflow within said cavity via said opening;
determining a volume of exhaled air flowing in said respiratory conduit;
detecting apnea events based on a change in said volume of exhaled air in subsequent patient breaths;
regulating to regulate the release of a controlled amount of a patient's exhaled breath based on the presence or absence or an apnea event.

18. The method of claim 17, the control device further comprising:
a controlled volume contained within said controlled interior volume;
a control aperture dial with a plurality of apertures therein, said apertures allowing a predetermined amount of exhaled breath from the patient to escape from the respiratory conduit while retaining a predetermined fraction of the exhaled breath to reintroduce to the patient during the next inhale.

19. The method of claim 18, further comprising:
a stepper motor operably connected to said control device to control a position of said control device based on an instruction from said controller.

* * * * *